United States Patent [19]
Liu et al.

[11] Patent Number: 6,007,715
[45] Date of Patent: Dec. 28, 1999

[54] APPARATUS FOR MAGNETIZING LIQUID MATTER

[76] Inventors: Yung-Sheng Liu; H. S. Yang, both of No. 85-5, Ta-Pien-Tou, Hou-Tsuo Tsun, Sanchih Hsiang, Taipei County, Taiwan

[21] Appl. No.: 09/153,043

[22] Filed: Sep. 15, 1998

[51] Int. Cl.⁶ ........................................................ C02F 1/48
[52] U.S. Cl. ............................ 210/222; 123/536; 123/538
[58] Field of Search ........................................ 210/222, 695;
123/538, 536; 335/302, 304, 306; 209/213,
223.1, 232, 215, 214

[56] References Cited

U.S. PATENT DOCUMENTS 4,956,084  9/1990  Stevens ..................................... 210/222
5,254,247  10/1993  Kashani ..................................... 210/222

*Primary Examiner*—W. L. Walker
*Assistant Examiner*—Marianne S. Ocampo
*Attorney, Agent, or Firm*—Rosenberg, Klein & Lee

[57] ABSTRACT

An apparatus for magnetizing liquid matter including two magnetically conductive, substantially U-shaped shells connected together, two magnets mounted in the shells between upright side walls of the shells, two pairs of aluminum packing strips respectively mounted around the magnets within the shells, a packing resin covered over the shells and the magnets and filled in gaps within the shells around the magnets, and a curved liquid delivery pipe mounted in between the packing resin coated magnets within the shells for permitting a liquid carried therein to be magnetized by magnetic lines of force emitted from the magnets.

1 Claim, 9 Drawing Sheets

6,007,715

APPARATUS FOR MAGNETIZING LIQUID MATTER

BACKGROUND OF THE INVENTION

The present invention relates to an apparatus for magnetizing liquid matter, more particularly to such a liquid matter magnetizing apparatus which is practical for use in a motor vehicle to magnetize fuel oil for complete combustion.

In 1970, scientists started researching the effect of a magnetic field in changing the chemical and physical properties of a liquid matter. In 1980, various magnetic apparatus have been developed for commercial use. It is well known that magnetic lines of force can: (1) activate hydrogen in fuel oil, so as to increase the chance of the contact between carbon and oxygen; (2) improve the solubility of water and reduce its surface tension; (3) activate oxygen in air; (4) charge the body of human beings to keep anions and cathions in a balanced manner; (5) activate drinking water, enabling magnetized drinking water to effectively carry waste and toxic matter out of the body and to help blood circulation; and (6) to help farm products grow quickly, so as to increase the productivity.

FIG. 8 shows an apparatus mounted around an oil pipe 5 to magnetize fuel oil delivered in the oil pipe 5. This apparatus comprises of two semi-circular shells 6 mounted around the oil pipe 5, the shells 6 having end flanges 63 respectively fastened together by screws, a plurality of magnets 61 packed in the shells 6 by a polymeric packing resin 62 and arranged around the oil pipe 5 with the S pole closely attached to the periphery of the oil pipe 5. This design cannot effectively shield the magnetic lines of force from escaping out of the apparatus (see FIG. 9). According to tests, the intensity of magnetic field measured at the diameter of the oil pipe does not surpass 0.002 Tesla when the oil pipe is designed having the diameter of 60 mm (see FIG. 10).

SUMMARY OF THE INVENTION

The present invention has been accomplished to provide an apparatus for magnetizing liquid matter which eliminates the drawback of the aforesaid prior art apparatus. According to the preferred embodiment of the present invention, the apparatus for magnetizing liquid matter comprises two magnetically conductive, substantially U-shaped shells connected together, the shells each comprising a flat base, and two upright side walls bilaterally connected to the flat base; two rectangular magnets respectively mounted in the shells between the upright side walls of the shells; two pairs of aluminum packing strips respectively mounted around the magnets within the shells; a packing resin covered over the shells and the magnets and filled in gaps within the shells around the magnets, permitting a through hole to be defined within the shells between the magnets; and a curved liquid delivery pipe mounted in the through hole within the shells between the magnets for permitting a liquid carried therein to be magnetized by magnetic lines of force emitted from the magnets.

DETAILED DESCRIPTION OF THE PREFERRED EMBODIMENT

Figure 1:
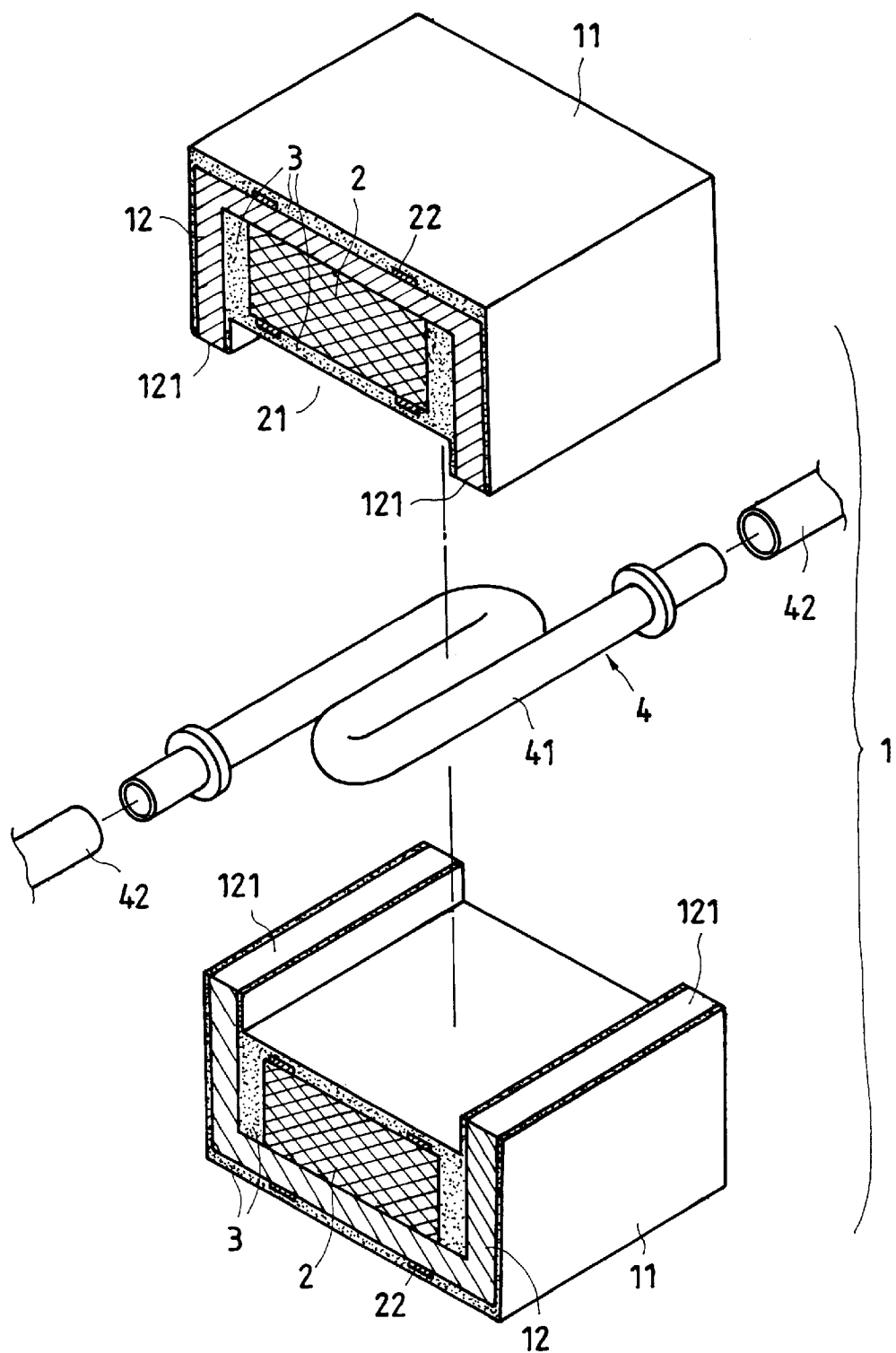
FIG. 1 is an exploded view of the preferred embodiment of the present invention.
Figure 2:
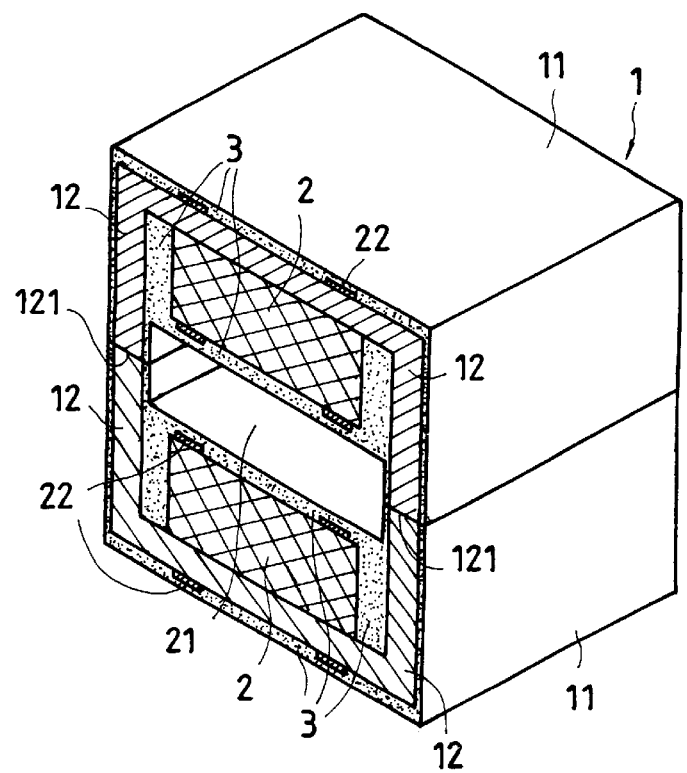
FIG. 2 is a sectional elevation of the preferred embodiment of the present invention (before the installation of the curved fuel oil delivery pipe.
Figure 3:
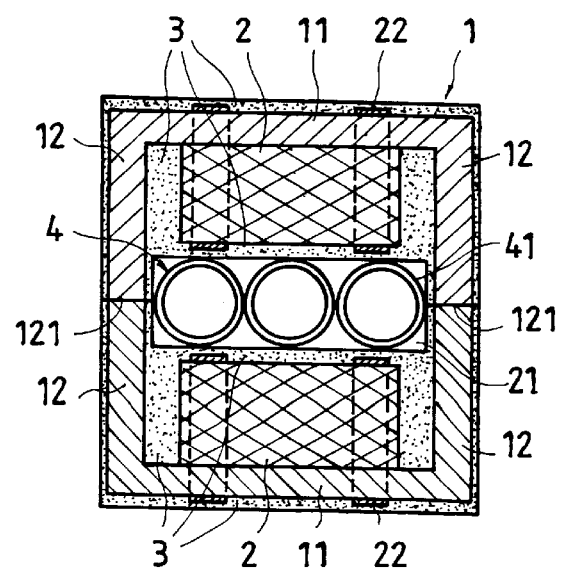
FIG. 3 is a cross sectional view of the preferred embodiment of the present invention.
Figure 4:
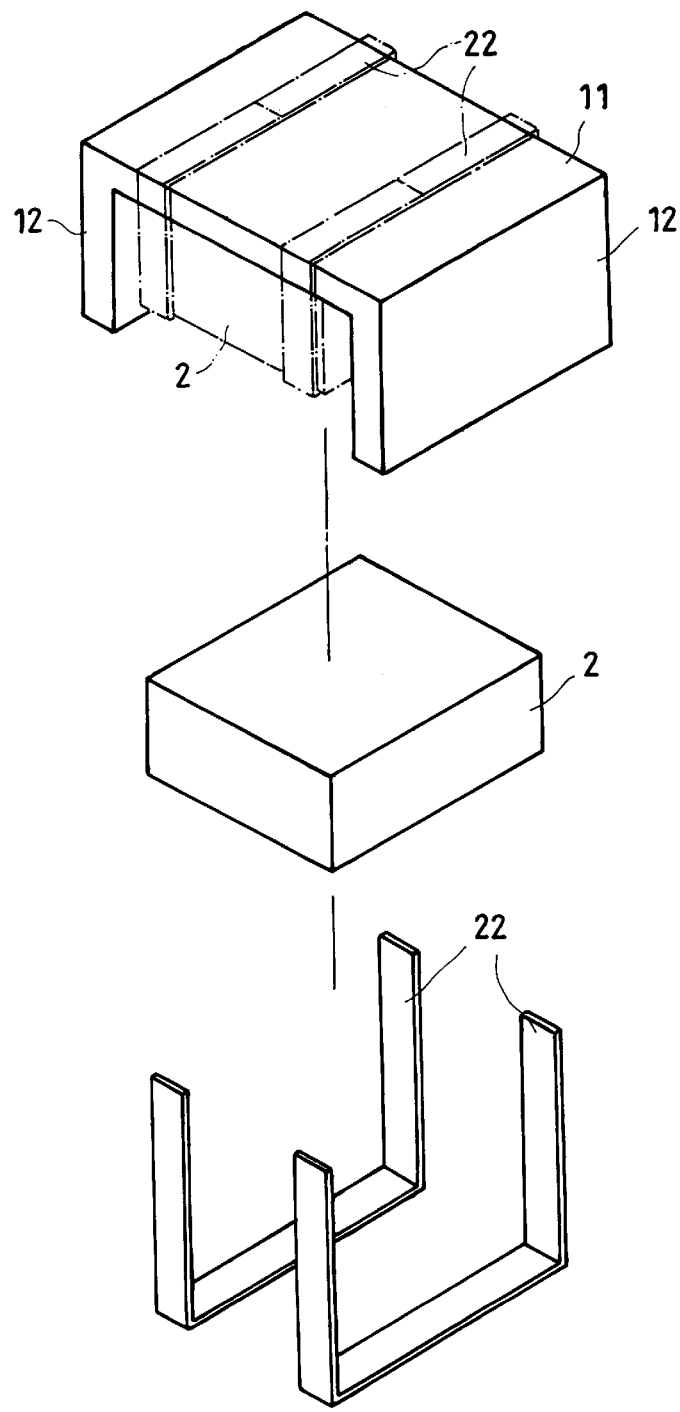
FIG. 4 is a schematic drawing showing the arrangement of the aluminum packing strips, the magnet and the shell according to the present invention.

Referring to FIGS. from 1 through 4, the apparatus 1 comprises two magnetically conductive, substantially U-shaped metal shells 11 fastened together, and two rectangular magnets 2 respectively mounted in the metal shells 11. Each metal shell 11 comprises two flat, upright side walls 12 respectively perpendicularly raised from two opposite short sides of the flat, rectangular base thereof. Each magnet 2 is packed with two aluminum packing strips 22. The aluminum packing strips 22 are mounted around the respective magnet 2, and arranged in parallel. When the magnet 2 with the respective aluminum packing strips 22 are in one metal shell 11, the assembly is covered with a packing resin 3. The outside surface of the magnet 2 and the outside surface of the metal shell 1 are covered by the packing resin 3, and the gaps between the magnet 2 and the upright side walls 12 of the shell 1 are filled up by the packing resin 3, however the end edges 121 of the upright side walls 12 are not covered by the packing resin 3. When the shells 11 are respectively attached together, the end edges 121 of the upright side walls 12 of one shell 11 are respectively maintained in close contact with the end edges 121 of the upright side walls 12 of the other. When the shells 11 are attached together, a through hole 21 is defined within the shells 11 between the magnets 2. A curved fuel oil delivery pipe 4 which has several turns 41 is mounted in the through hole 21, and connected between two pipe sections 42 of a motor vehicle fuel pipe.

Figure 5:
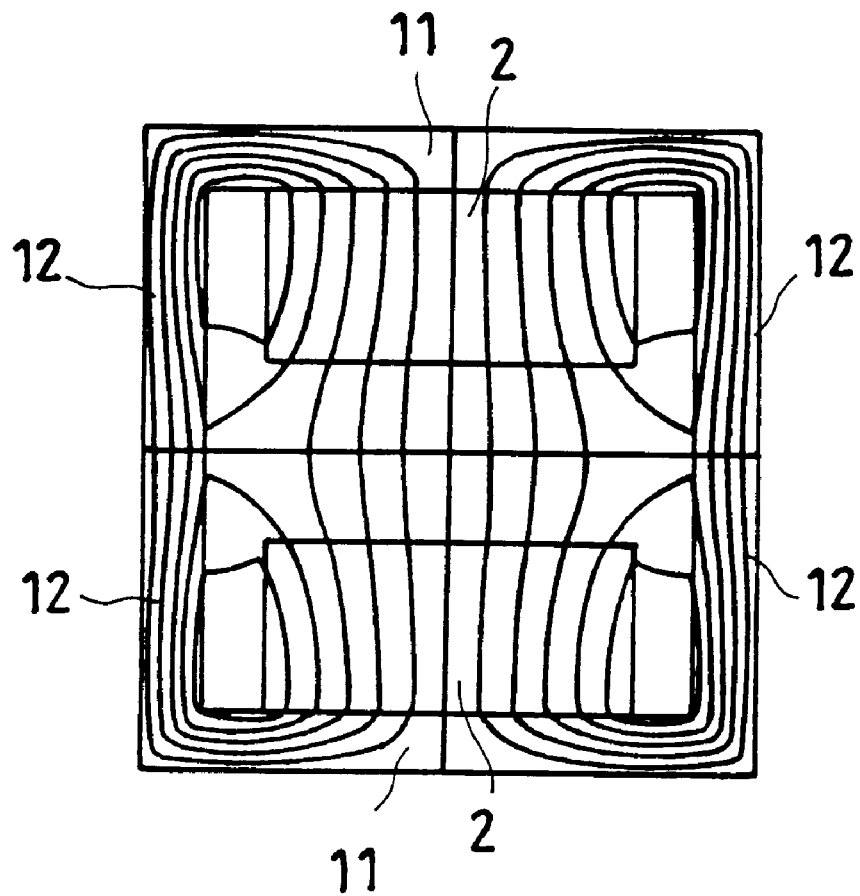
FIG. 5 illustrates the distribution of magnetic lines of force in the apparatus for magnetizing liquid matter according to the present invention.
Figure 6:
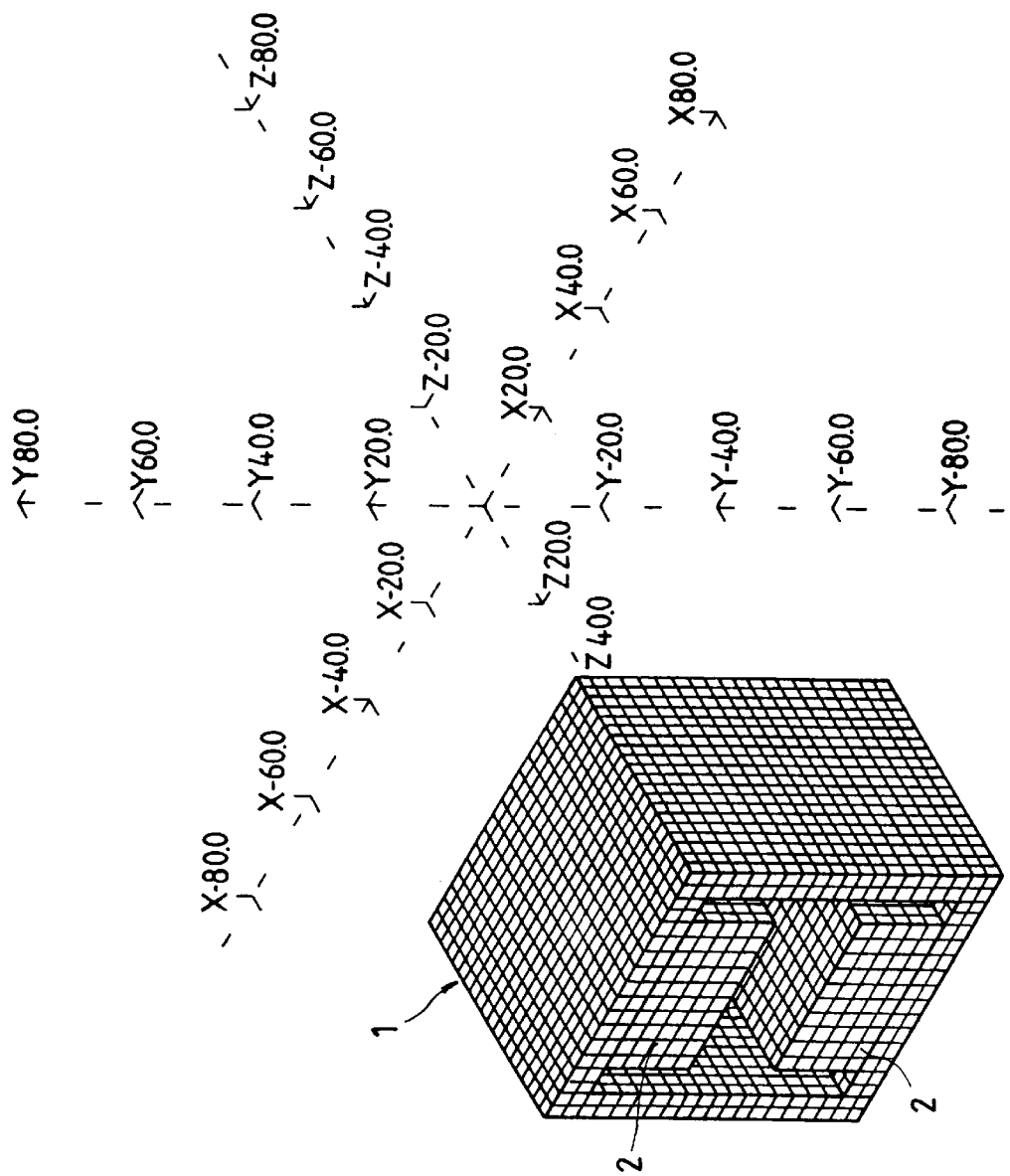
FIG. 6 is a magnetic lines of force distribution chart drawn by computer according to the present invention.
Figure 7:
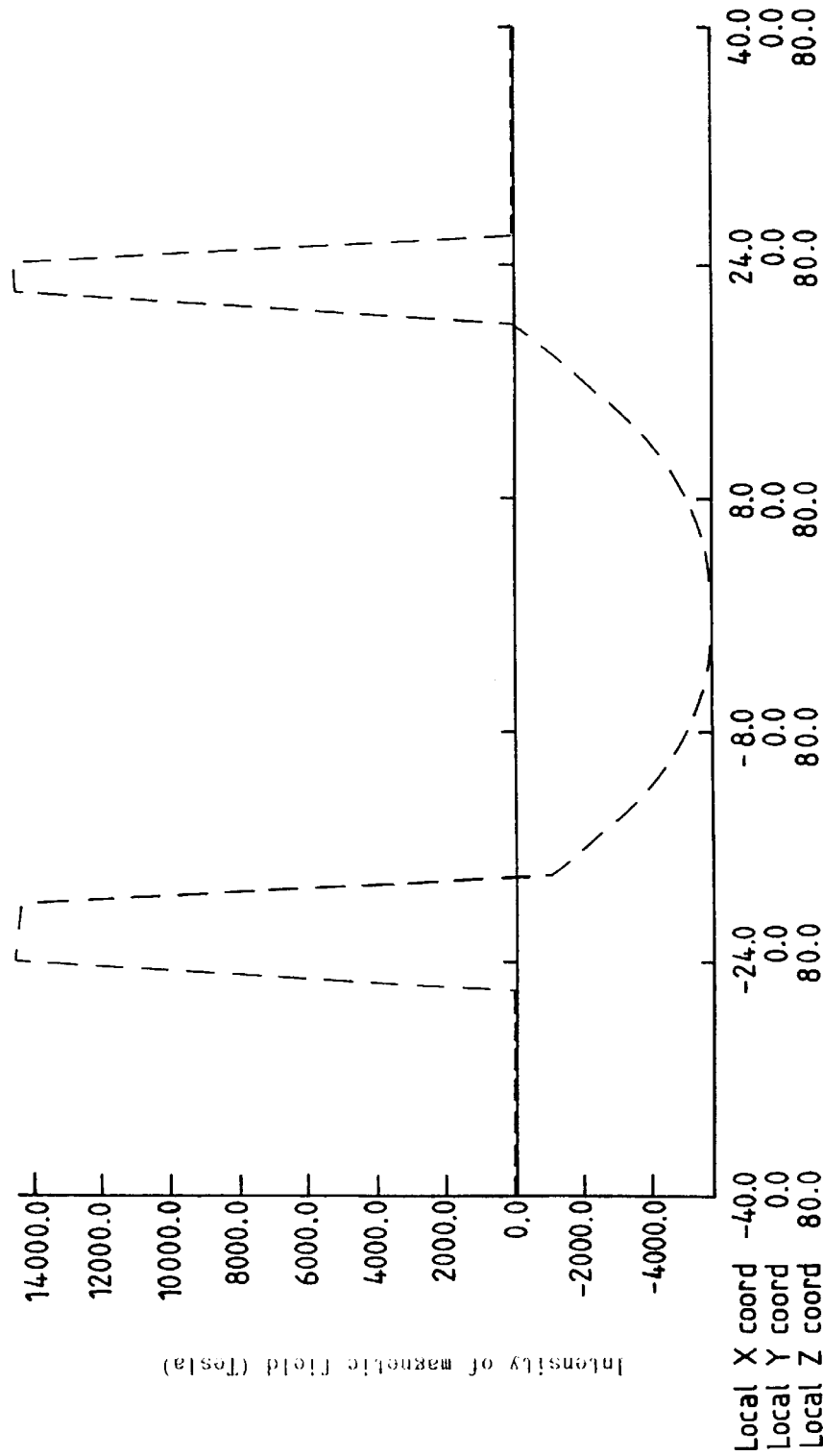
FIG. 7 is a magnetic field intensity curve obtained according to the present invention.
Figure 8:
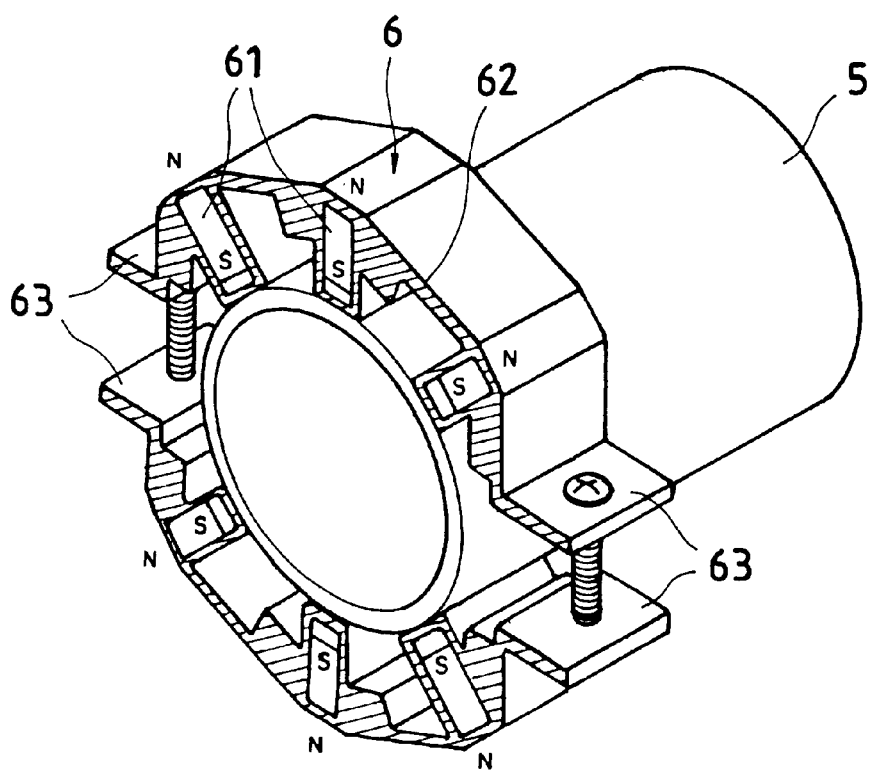
FIG. 8 is a sectional elevation of an apparatus for magnetizing liquid matter according to the prior art.
Figure 9:
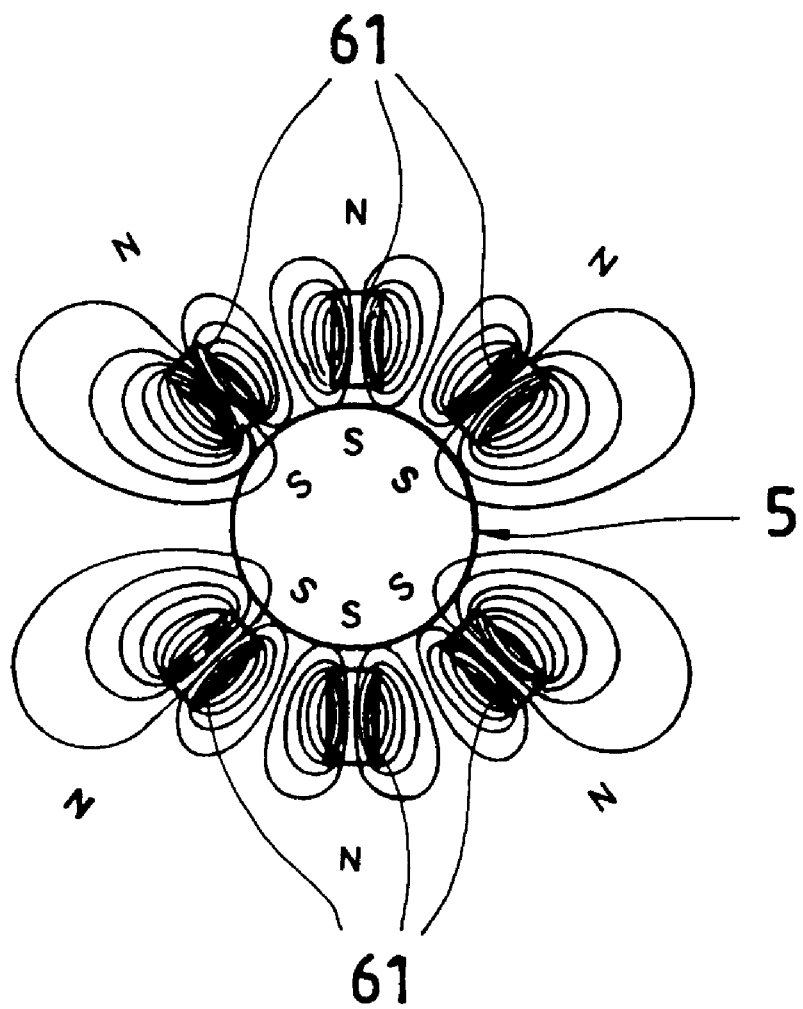
FIG. 9 is a magnetic lines of force distribution chart drawn by computer according to the prior art.
Figure 10:
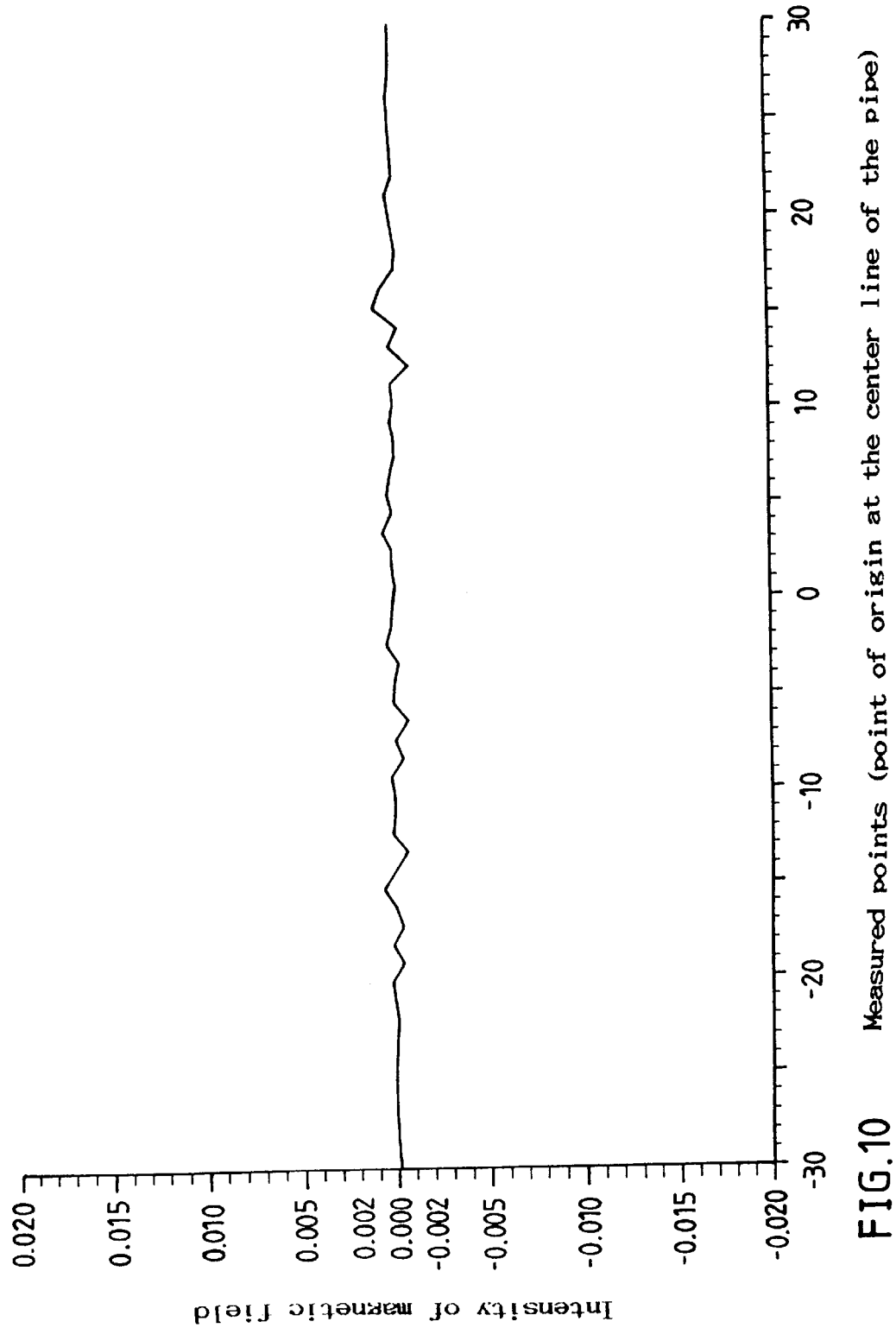
FIG. 10 is a magnetic field intensity curve obtained according to the prior art.

Referring to FIGS. 5 and 6 and 7 and FIG. 3 again, magnetic lines or force are guided from the magnets 2 through the shells 11, therefore magnetic lines of force are evenly distributed in the apparatus 1 and pass through the curved fuel oil delivery pipe 4 to magnetize fuel oil.

While only one embodiment of the present invention has been shown and described, it will be understood that various modifications and changes could he made thereunto without departing from the spirit and scope of the invention disclosed.

What the invention claimed is:

1. An apparatus for magnetizing liquid matter comprising:
   two magnetically conductive, substantially U-shaped shells connected together, said shells each comprising a flat base, and two upright side walls bilaterally connected to said flat base;
   two rectangular magnets respectively mounted in said shells between the upright side walls of said shells;
   two pairs of aluminum packing strips respectively mounted around said magnets within said shells;

a packing resin covered over said shells and said magnets and filled in gaps within said shells around said magnets, permitting a through hole to be defined within said shells between said magnets; and a curved liquid delivery pipe mounted in the through hole within said shells between said magnets for permitting a liquid carried therein to be magnetized by magnetic lines of force emitted from said magnets, said curved liquid delivery pipe having a plurality of turns arranged within said through hole.

* * * * *